United States Patent
Vijayan et al.

(10) Patent No.: US 11,027,272 B1
(45) Date of Patent: Jun. 8, 2021

(54) TRANSFER DISPENSERS FOR ASSAY DEVICES

(71) Applicant: Plexium, Inc., San Diego, CA (US)

(72) Inventors: Kandaswamy Vijayan, San Diego, CA (US); Kapil Mahakalkar, San Diego, CA (US); Yi Zhang, San Diego, CA (US)

(73) Assignee: Plexium, Inc., San Diego, CA (US)

( * ) Notice: Subject to any disclaimer, the term of this patent is extended or adjusted under 35 U.S.C. 154(b) by 0 days.

(21) Appl. No.: 16/774,871

(22) Filed: Jan. 28, 2020

(51) Int. Cl.
*B01L 3/00* (2006.01)

(52) U.S. Cl.
CPC ....... *B01L 3/5025* (2013.01); *B01L 2200/025* (2013.01); *B01L 2200/0652* (2013.01); *B01L 2300/046* (2013.01); *B01L 2300/0893* (2013.01)

(58) Field of Classification Search
None
See application file for complete search history.

(56) References Cited

U.S. PATENT DOCUMENTS

| | | | | |
|---|---|---|---|---|
| 2002/0137199 A1* | 9/2002 | Jobin | .................. | B01L 3/0293 435/287.2 |
| 2003/0021734 A1* | 1/2003 | Vann | .................. | B01J 19/0046 506/23 |
| 2010/0068793 A1* | 3/2010 | Ungrin | .................. | C12N 5/0606 435/283.1 |
| 2010/0200405 A1* | 8/2010 | Lenz | .................. | B03C 1/0332 204/600 |
| 2012/0276654 A1* | 11/2012 | Heavner | .................. | B01L 3/0275 436/177 |
| 2019/0143328 A1* | 5/2019 | Savran | .................. | B01L 3/502761 435/5 |
| 2019/0358629 A1 | 11/2019 | Vijayan et al. | | |

OTHER PUBLICATIONS

Lu, C. et al. (Mar. 2018, e-published Jul. 28, 2017) "Stimuli-responsive polymer nano-science: Shape anisotropy, responsiveness, applications," *Prog. Polym. Sci., Stimuli Responsive Polymers*, vol. 78, pp. 24-46.

Taresco, V. et al. (2018). "Stimuli-Responsive Prodrug Chemistries for Drug Delivery," *Adv. Therap.*, 1, 1800030, 14 ages. Wiley Online Library. onlinelibrary.wiley.com/doi/full/10.1002/adtp.201800030.

* cited by examiner

*Primary Examiner* — Jill A Warden
*Assistant Examiner* — Brittany I Fisher
(74) *Attorney, Agent, or Firm* — Mintz Levin Cohn Ferris Glovsky and Popeo, P.C.

(57) ABSTRACT

Disclosed are transfer dispensers for assay devices. These dispensers provide for transfer of a single assay component into a single well in the assay device. This ensures that the assay conducted in each well contains only a single component.

29 Claims, 8 Drawing Sheets

TRANSFER DISPENSERS FOR ASSAY DEVICES

FIELD

This disclosure describes transfer dispensers for assay devices. These dispensers provide for transfer of a single assay component into a single well in the assay device per use. This ensures that the assay conducted in each well contains only a single unit of that component.

STATE OF THE ART

Combinatorial libraries are well known in the literature and often utilize beads, where each bead contains multiple copies of a single compound bound by a linker to the bead. In addition, the bead typically contains a reporting element such as DNA that allows for assessing the structure of the single compound on the bead. Many of these libraries are limited by the fact that the compound being tested remains on the bead during the assay. As such, the biological data generated by the assay is potentially compromised by the possibility that the bound compound is not able to effectively bind to the target of choice. This could be due to physical interference arising from the bead as well as possible steric interference due to the attachment of a linker connecting the compound to a bead. As to the latter, this linkage could inhibit the ability of an otherwise potent compound from binding properly to the target thereby providing assay results that evidence less than the actual potency of the compound. Moreover, when the target is a cell and penetration of the compound into the cell is required as part of the assay, compounds remaining bound to the bead are unlikely to penetrate into the cell.

One option for addressing this problem includes the use of cleavable linkers that cleave under proper stimulation (e.g., light) thereby freeing the compound from the bead. Once the compound is in solution, such as in a test well, it is free to orient itself in a manner that provides maximum potency in the assay. Still further, release of these compounds can be conducted in a manner such that the amount of compound released is controlled so as to provide meaningful dose dependent data. See, e.g., US Patent Application Pub. No. 2019/0358629, which is incorporated herein by reference in its entirety.

In a typical combinatorial library, thousands of beads are used where each bead contains multiple copies of the same test compound. Such beads can be made by the well-known split/pool synthetic processes. In one case, the identity of the compound on the bead is recorded by a reporter molecule such as DNA. In another case, the identity of each reaction step conducted on each bead is recorded by the addition of a DNA segment corresponding to that step thereby generating a unique strand of DNA for each compound. Typically, each well comprises a single bead as well as other assay components such as a single mammalian cell. If a given well in the assay device provides for a positive "hit" (an active compound), the DNA is recovered, amplified and then sequenced. The resulting sequence is the aggregate of the specific reaction steps used to synthesize that compound thereby allowing the synthetic chemist to ascertain the structure of the active compound.

SUMMARY

In order to increase the amount of information generated by an assay, one option is to increase the number of wells in the assay device (e.g., a high throughput device). In general, assay devices that contain ten (or more) thousand to millions of wells will provide more information as to what structures provide activity against a given target as opposed to assay devices that contain tens to hundreds of wells.

Moreover, in order to accommodate an aqueous solution and other assay components, the well size must be much larger than the assay components such as a bead. This makes adding only a single small bead to a single well a serious challenge. If by chance, two or more beads each containing different compounds are added to a single well, the ability to assess which compound is active (or if both are active) becomes problematic at best. When the assay device contains thousands to millions of individual wells, the ability to add just a single bead to each well is a huge challenge. Adding to that complication is how to add a single assay component to each well when the assay requires the addition of two different components (e.g., a single bead and a single cell in a single well).

Accordingly, there is an ongoing need to provide dispensers for addition of a single assay component to a single well in a high throughput assay device.

In one embodiment, there is provided a dispenser (1) comprising a multiplicity of cavities (2) wherein each cavity (2) is configured to reversibly hold/capture only a single assay component (3), such as a bead (10), and further wherein the dispenser (1) is configured to fit or mate with an assay device (20) comprising a multiplicity of wells (21) such that, when fitted, each cavity (2) in said dispenser (1) is aligned with a single well (21) in said assay device (20). Upon release, assay components (3) move from dispenser (1) into assay device (20) such that a single assay component (3) is deposited into a single well (2).

In one embodiment, cavities (2) in dispenser (1) are configured to retain only a single assay component (3). In one embodiment, assay component (3) is a bead (10) which comprises a multiplicity of the same compound reversibly linked thereto by a cleavable linker and optionally a DNA reporter that records either the structure of the test compound bound thereto or the synthetic steps used to create the test compound.

In one embodiment, assay component (3) comprises a mammalian cell such as a human cell which is integral to the assay to be conducted.

BRIEF DESCRIPTION OF THE FIGURES

FIGS. 5A and 5B illustrate loading of assay component (3) into an empty dispenser (1).

FIG. 6A1 is based on FIG. 6A with the optional gap (22) removed.

FIG. 6B1 is based on FIG. 6B with the optional gap (22) removed.

DETAILED DESCRIPTION

Disclosed are dispensers for loading assay components into an assay device (20) capable of assaying library of test compounds generated by combinatorial chemistry techniques. However, prior to describing this invention in more detail, the following terms will first be defined. If not defined, terms used herein have their generally accepted scientific meaning.

For ease of reference, the numerous apparatus and numbers used herein are summarized as follows:

Dispensers

Figure 1:
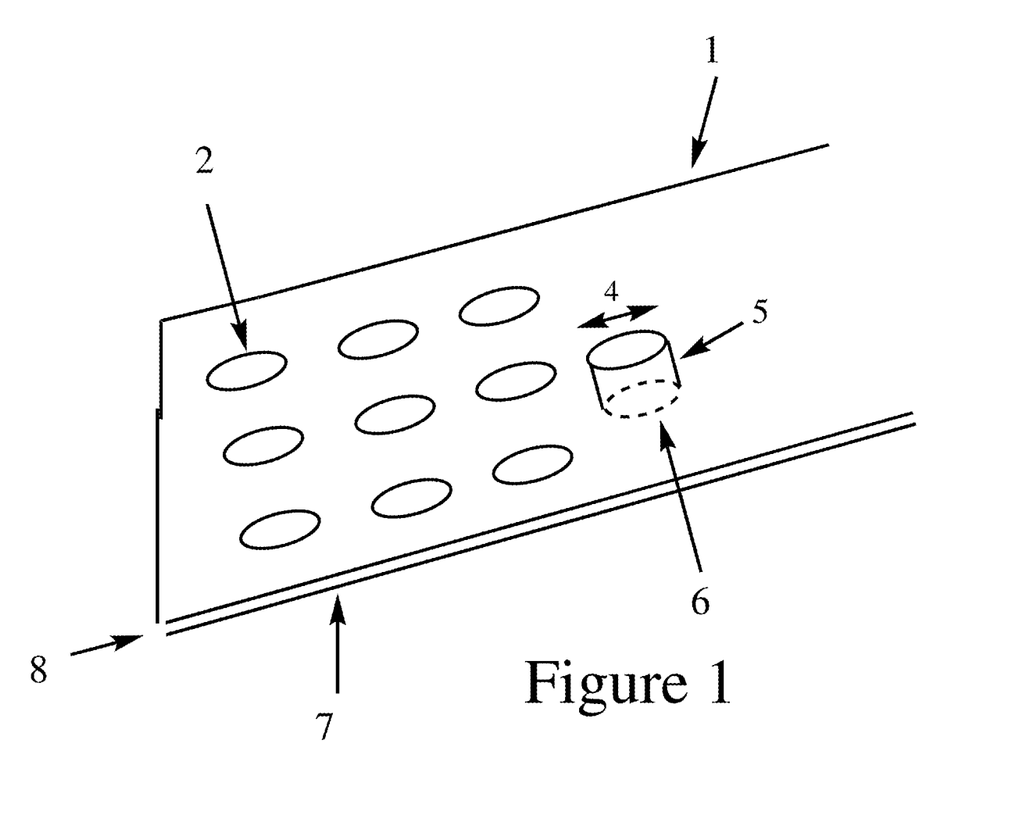
FIG. 1 illustrates a top view of dispenser (1) having a bottom surface (7) including cavities (2) and where one cavity (2) is shown in three-dimensions. That three-dimensional cavity (2) has bottom surface (6), a diameter (4) and a height (5).

Dispenser (1)—delivers assay components (3), such as bead(s) (10), to an assay device (20). Dispenser (1) comprises floor (7), cavities (2) and a thickness (8). As indicated in exemplary FIG. 1, cavities (2) have diameter (4), height (depth) (5), and a cavity floor (6). FIG. 1 shows an embodiments of dispenser (1) with one cavity (2) in expanded view. It should be understood that height (depth) (5) of this expanded cavity (2) is shown to be less than thickness (8). Any numbers recited herein that range from (1) to (9) correspond to a component of dispenser (1).

Beads

Beads (10) each comprise multiple copies of the same compound and may be magnetic or non-magnetic beads (10) having a diameter (11) and a height (12). When beads (10) are spherical, diameter (11) and height (12) are identical. Any numbers recited herein that range from (11) to (19) correspond to a component of bead (10). Beads (10) are an example of an assay component (3).

Assay Device

Assay device (20)—corresponds to a high throughput assay device containing a multiplicity of wells (21) where assays are conducted using a multiple copies of a single test compound. Any numbers recited herein that range from (21) to (29) correspond to a component of assay device (20).

Containment Cap

Containment cap (30)—corresponds to a cap that is sized to fit over dispenser (1). Containment cap (30) comprises an intake port (31) that delivers beads (10) to dispenser (1) resulting in a single bead (1) in each cavity (2). Containment cap (30) optionally has an outlet port (32) on its opposite side so as to retrieve beads (10) that are not captured by a cavity (2). Any numbers recited herein that range from (31) to (39) correspond to a component of containment cap (30).

Cell

Cell (40) is a mammalian cell such as a murine cell, a porcine cell, a primate cell (including a human cell), and the like. Cell (40) can be used in assay device (20) to assess the biological activity of a test compound. Any numbers recited herein that range from (41) to (49) correspond to a component of cell (40).

Magnet

Figure 4:
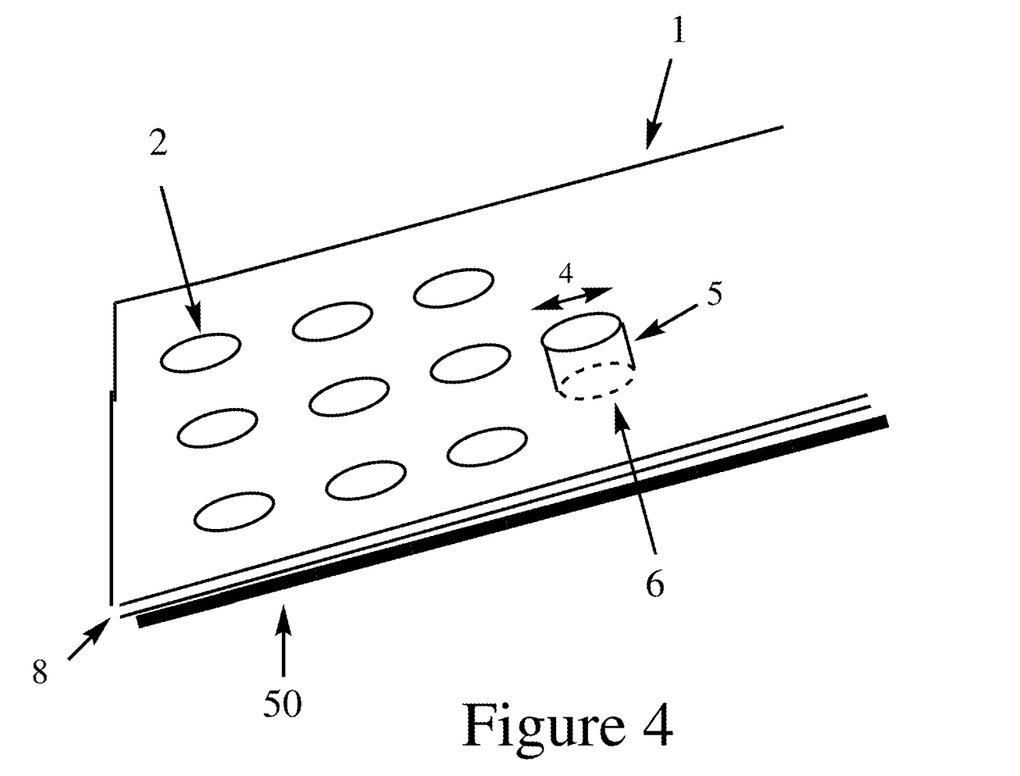
FIG. 4 illustrates assay component (3) which comprises a magnetically attractable bead (10) fitted into cavity (2) and held in place by magnet (50) removably fitted to the outside bottom (7) of dispenser (1).

Magnet (50) is illustrated in FIG. 4 attached to the bottom surface (7) of dispenser (1). Any numbers recited herein that range from (51) to (59) correspond to a component of magnet (50).

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others.

"Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

"Consisting of" shall mean excluding more than trace elements of other ingredients and substantial method steps. Embodiments defined by each of these transition terms are within the scope of this invention.

The term "assay device" refers to a device that is capable of simultaneously assaying multiple test compounds each in a single well against a target. Such devices contain a multiplicity of wells where each well preferably contains multiple copies of substantially the same compound. The device comprises a very large number of wells. In one embodiment, the number of wells ranges from about 5,000 to about 2,000,000. In one embodiment, the well density on the device is at least 10 wells per square millimeter and the number of wells is at least about 5,000.

The term "assay component" refers to micron sized, shaped components that are used in conducting a particular assay. In one embodiment, the assay component is a bead. In another embodiment, the assay component is a mammalian cell. In yet another embodiment, the assay component includes both beads and cells.

The term "bead" refers to beads (10) well known in the art for use in combinatorial chemistry. In one embodiment, the surface of bead (10) comprises a multiplicity of the same test compound bound thereto through a cleavable linker. Beads (10) may also comprise DNA barcodes that record the structure of the test compound or the synthetic steps used to synthesize the compounds. These barcodes are attached to beads (3) either by cleavable or non-cleavable linker. If the barcodes are attached via a cleavable linker, then preferably, the cleavable linker used with the barcodes is cleaved by a mechanism different from that of the test compound.

In another embodiment, bead (10) contains multiple copies of the same reporter molecule. One example of a reporter molecule is a fluorescent molecule linked to bead (10) via a cleavable linker. Preferably, the reporter molecule is attached using the same cleavable linker that is used to bind the test compound to bead (10). When so used, bead (10) may include a quencher molecule that is bound proximate to the fluorescent molecule on bead (10) so as to attenuate the fluorescence generated. Typically, the quencher molecule is bound to the bead by either a non-cleavable bond or by a cleavable bond that is cleaved by a mechanism that is different than the cleavable linker used to bind the fluorescent molecule to the bead.

Alternatively, the quencher is bound to the bead by the same linker used to bind the test compound to the bead. In this embodiment, the fluorescent compound is bound to the linker by a non-cleavable bond or by a cleavable bond that is cleaved by a mechanism that is different from the cleavable linker used to bind the quencher to the bead.

During an assay, knowledge of the extent of test compound released from bead (10) by a stimulus that cleaves the cleavable bond may be essential to that assay. Using bead (10) with a reporter molecule can provide that knowledge by measuring the change in fluorescence generated by decoupling the fluorescent compound away from the quencher against a standard curve.

For example, when the reporter molecule and the test compound are bound to the bead by the same cleavable linker, release of the test compound by the stimulus that breaks the cleavable linker will also release the reporter molecule in the same quantifiable manner. In doing so, the reporter molecule and the quencher are decoupled and the resulting change in fluorescence correlates to the amount of test compound released. See, e.g., US Patent Application Pub. No. 2019/0358629 which is incorporated herein by reference in its entirety.

Alternatively, when the quencher molecule and the test compound are bound to the bead by the same cleavable linker, release of the test compound by the stimulus that breaks the cleavable linker will also release the quencher in the same quantifiable manner. In doing so, the reporter molecule and the quencher are decoupled and the resulting change in fluorescence correlates to the amount of test compound released.

In another alternative embodiment, the quencher molecule, the test compound and the reporter compound are all attached to bead (10) by the same cleavable linker such that all of these are cleaved from bead (10) by the applied stimulus. In doing so, the reporter molecule and the quencher molecule become decoupled from each other in the aqueous environment of the assay. This results in a change in fluorescence that correlates to the amount of the test compound released.

Beads (10) are typically polymeric in form albeit with some also comprising sufficient $Fe_3O_4$ to render them susceptible to magnetic attraction. Numerous beads (10) are commercially available and have varying sizes, e.g., about 0.1 microns to 10 or more microns including amino functionalized beads, carboxyl functionalized beads, magnetic beads with functional groups, etc. See, for example, Spherotech, Inc., Lake Forest, Ill., USA, and Agilent, Inc., Santa Clara, Calif., USA. These beads are readily functionalized to contain a test compound and/or a reporter molecule using conventional chemistry well known in the art. It is understood that beads with a nominal diameter of 5 microns include beads that are smaller and larger than 5 microns with the number average being 5 microns. In order to avoid multiple beads (40) being placed into a single well (10), one can exclude smaller beads by size exclusion filtration using a filter that passes beads below a set diameter while retaining beads above that diameter. Accordingly, in some embodiments, a bead size of 5 microns refers to beads where the beads have been filtered to remove substantially all of the beads that are smaller than 5 microns. Such beads are referred to herein as "size excluded beads". In all cases, such size excluded beads are preferred.

In one embodiment, the assay component (3) is a viable mammalian cell such as a human cell. This cell is used in the assay to assess the biological activity, if any, of a given test compound. Assays using mammalian cells are well known in the art. Suitable cells include cancer cells, beta cells responsible for insulin expression, neurons, and the like.

The term "test compound" means a compound releasably bound to a bead (10) that, when released, is to be tested for biological activity in an assay conducted in well (21) of assay device (20).

The term "releasably bound" means that a test compound bound to bead (10) can be released by application of stimuli that breaks the bond. Such bonds are sometimes referred to herein as "cleavable" bonds. The art is replete with examples of cleavable bonds and the appropriate stimulus that breaks that bond. Non-limiting examples of cleavable bonds include those that are released by pH changes, enzymatic activity, oxidative changes, redox, UV light, infrared light, ultrasound, changes in magnetic field, to name a few. A comprehensive summary of such cleavable bonds and the corresponding stimuli required to cleave these bonds is provided by Taresco, et al., Self-Responsive Prodrug Chemistries for Drug Delivery, Wiley Online Library, 2018, onlinelibrary.wiley.com/doi/full/10.1002/adtp.201800030 which is incorporated herein by reference in its entirety.

The term "cavity" refers to a well or similarly shaped depression in the dispenser (1) that is sized to capture and hold assay component (3) as described herein. The size of cavity (2) is correlated to the size of assay component (3) so as to ensure that only one assay component is captured in a single cavity (2). Cavity (2) captures a single assay component (3) so that a single assay component (3) can be added to a single well in an assay device (20) in a reproducible manner. In one embodiment, the capturing mechanism of cavity (2) is gravity assisted based using the metrics of cavity (2) including diameter (4) and height (5) relative to the diameter and height of assay component (3). In other embodiments, capturing may be achieved by magnetic forces or by reversibly expandable polymers as described below.

When the capturing mechanism is based on the diameter (4) and height (5) of cavity (2), the size of the diameter (4) is generally less critical than the size of height (5). In general, diameter (4) is sized to allow only a single assay component (3) to reside in a single cavity (2). In one embodiment, diameter (4) is at least about 101% or more than the diameter of assay component (3). Preferably, diameter (4) of cavity (2) ranges from about 101% to about 150% of the diameter of assay component (3). Height (5) of cavity (2) also is selected such that only a single assay component can reside in a single cavity (2). In this embodiment, height (5) can range from about 50% to about 115% of the height of assay component (3). Stated another way, the top portion of assay component (3) can protrude out of cavity (2) provided that the component is held in that cavity. Sizes may be any value or subrange within the recited ranges, including endpoints.

Optionally, the capturing mechanism described above can be achieved by employing a reversibly expandable polymer such that the size of cavity (2) can change from a non-expanded state to an expanded state. In the non-expanded state, the diameter (4) of cavity (2) can be less than that of assay component (3) provided that in the expanded state, diameter (4) of cavity (2) is at least about 100.1% or more of the diameter of the assay component to be added. Such reversibility of polymer size is disclosed by Lu, et al., *Prog. Polym. Sci.*, Stimuli Responsive Polymers, 2017, cecas.clemson.edu/urbanresearch/stimuli-responsive-polymers/, which is incorporated herein by reference in its entirety.

In a preferred embodiment, the diameter (4) of expanded cavity (2) in such dispensers (1) ranges from 100.1 to about 115 percent of the diameter of assay component (3) whereas the height (5) of expanded cavity (3) ranges from about 50 to about 115 percent of the height of assay component (3). Stated another way, height (5) of cavity (2) can allow a portion of assay component (3) to protrude out of cavity (2) provided that assay component (3) is held in that cavity. Sizes may be any value or subrange within the recited ranges, including endpoints.

Optionally, when the assay component (3) is a bead (10) comprising $Fe_3O_4$, the capturing mechanism described above can be achieved by employing a magnet (50) that is placed beneath the bottom surface (7) of dispenser (1) after loading the beads into cavities (2). In a preferred embodiment, diameter (4) of cavity (2) ranges from about 100.1 to about 150 percent of the size of beads whereas height (5) can range from about 50% to 115% of the height of bead. Sizes may be any value or subrange within the recited ranges, including endpoints. One preferred class of beads are those of mixed iron/silica core ($Fe_3O_4/SiO_2$). Such beads are known in the art and are commercially available from EPRUI Biotech, Inc.—see, e.g., www.nanoparticles-microspheres.com/product/magnetic-silica-microspheres.html.

Regardless of the capturing mechanism employed, the maximum diameter (4) and height (5) of each cavity (2) is such that it can only accept a single assay component (3). Stated otherwise, diameter (4) and height (5) of each cavity (2) is sized such that it cannot hold more than one assay component (3). In one preferred embodiment, the maximum diameter (4) of cavity (2) ranges up to about 150% of the diameter of assay components (3) to be added to dispenser (1). More preferably, the diameter (4) of cavities (2) are from 101% to 125% of the diameter of assay component (3) with the understanding that for reversibly expandable cavities, the size of such cavities (2) is measured in the expanded state. Likewise, the maximum height of cavity (2) is ranges up to about 150% and preferably 125% of the height of assay component (3). The minimum height of cavity (2) is about 50% of the height of assay component (3). Sizes may be any value or subrange within the recited ranges, including endpoints.

Still further, it is understood that the diameter (4) of assay component (3) is measured along the longest axis of that component. While it is preferred that a substantially spherical assay component (3) is used where the longest axis is uniform throughout, other shapes can be used. One such non-spherical shape useful herein is an orbiform which is solid having a uniform width throughout and is capable of rolling. Still other shapes that are useful herein are elliptical (3) shapes. Preferred elliptical shapes are those having a ratio of long axis to short axis of greater than 1 and less than 1.5 and preferably less than 1.2.

Dispenser

Figure 5A:
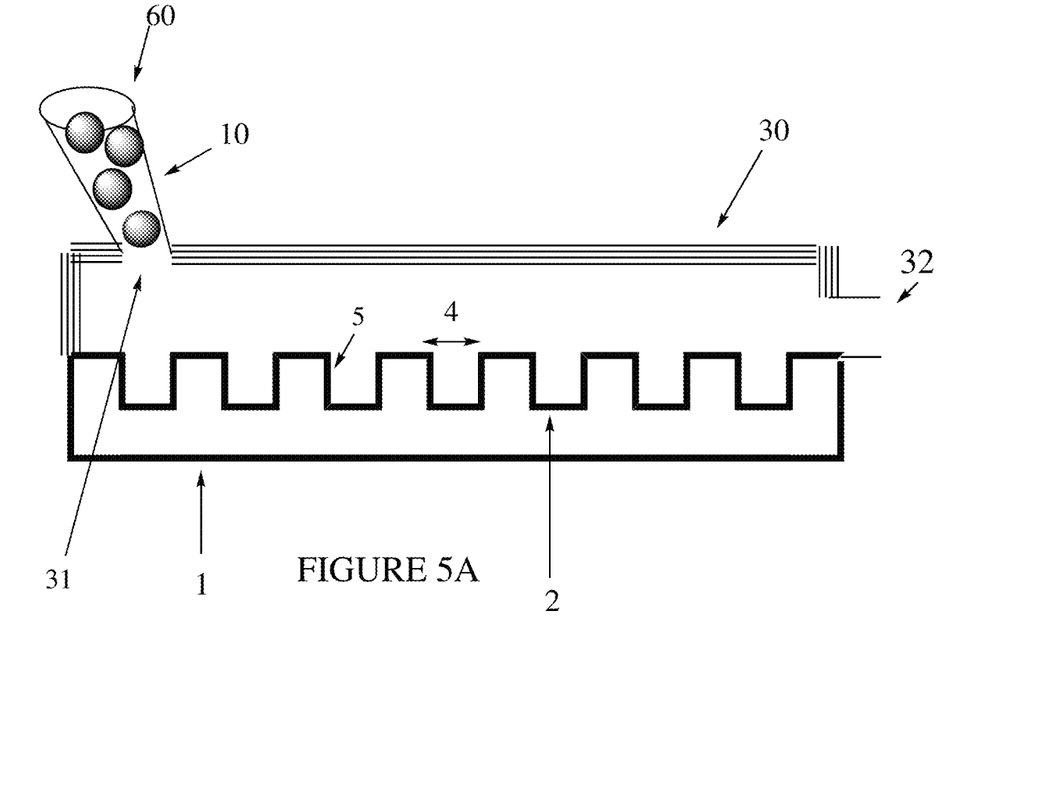
FIG. 5A illustrates a containment cap (30) equipped with an inlet (31) and outlet (32) used in conjunction with a funnel-like cone (60) to deliver beads (10) into wells (2) of dispenser (1).
Figure 5B:
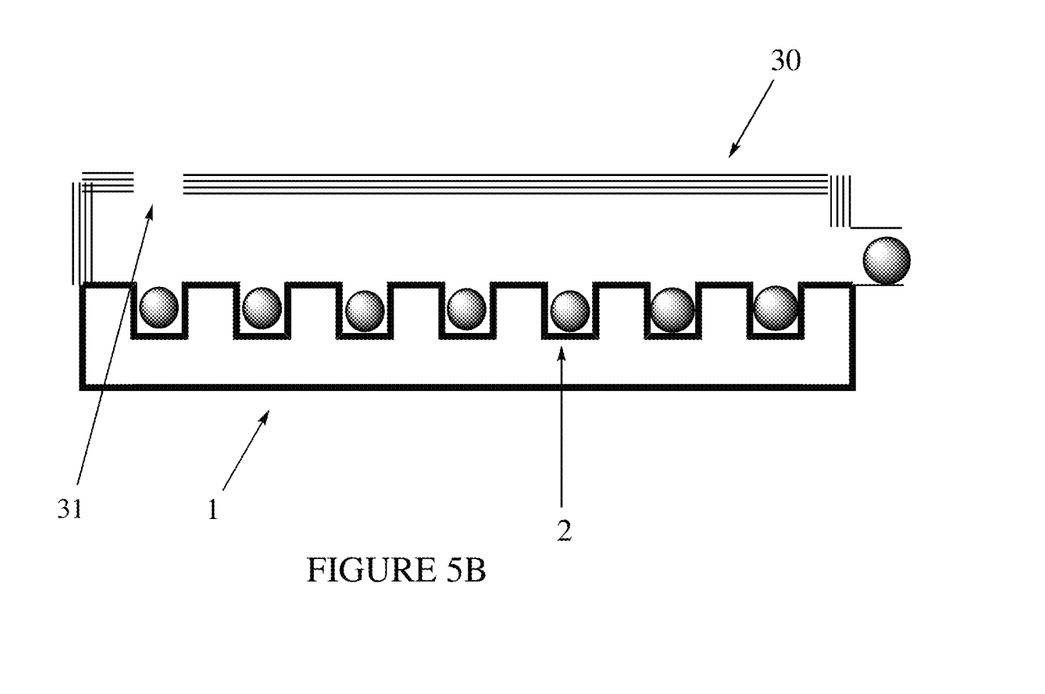
FIG. 5B illustrates beads (10) delivered into cavities (2) of dispenser (1). Extra beads not within a cavity (2) exit containment cap (30) to recycle into a separate dispenser (1) for analysis.

The ability to assay a very large combinatorial library of compounds entails as an initial step the delivery of a single assay component (3) into a single well (21) of assay device (20). In practice, there may be as many as 2+ million wells (21) incorporating into assay device (20). As shown in FIG. 5, the diameters of well (21) in these devices (20) are significantly larger than the diameter of cavities (2) of dispenser (1). Such a size differential makes adding a single assay component (3) into a single well (21) of assay component (3, shown as bead 10) a technically challenging endeavor.

Bead as the Assay Component

In this section, assay components (3) are beads (10). These beads are preferably spherical to substantially spherical and have a diameter of from about 0.5 to about 100 microns. FIG. 1 shows dispenser (1) having a plurality of cavities (2) and a bottom surface (7) and where one cavity (2) is shown in three-dimensions with a cavity height (5), a cavity diameter (4) and a cavity bottom (6).

In more general terms, dispenser (1) of FIG. 1 has a top to bottom thickness (8) that is preferably at least about 0.1 mm to about 5 mm and contains a multiplicity of cavities (2) on the top surface thereof. Thickness may be any value or subrange within the recited ranges, including endpoints. Dispenser (1) comprises any of a number biocompatible, materials including but not limited to polymers such as cyclo Olefin Polymer (COP) which is commercial available from ZEONEX, cyclic olefin copolymers (COC) which are commercially available from a number of sources such as Polyplastics USA, Inc. (Farmington Hillis, Mich., USA), polyimides which are commercially available from a number of sources such as Putnam Plastics (Dayville, Conn., USA), polycarbonates which are commercially available from a number of sources such as Foster Corporation (Putnam, Conn., USA), polydimethylsiloxane which are commercially available from Edge Embossing (Medford, Mass., USA) and polymethylmethacryate which is commercially available from Parchem Fine & Specialty Chemicals (New Rochelle, N.Y., USA).

Dispensers (1) described herein can be readily prepared by hot embossing methods which are well known in the art. Such hot embossing methods use a sheet of thermoplastic polymer which is heated to a temperature slightly higher than its glass transition temperature in order to soften the plastic. A stamp is selected that comprises a number of prongs placed in a desired pattern on its surface. Each prong is sized to have diameter and a depth correlating to the size of the cavities (2) described above. Preferred prongs are cylindrical in nature, but otherwise can be any shape desired. The stamp is sized so that the portion comprising the prongs fits within the top surface of the sheet. Sufficient force is applied to the stamp so as to ensure that the full length of the prongs sink into the sheet. The force required is dependent on the degree of softness of the sheet and is readily ascertainable by the skilled artisan. As the sheet cools, the prongs are removed so as to provide for a sheet now containing cavities (2) as per FIG. 1.

Alternatively, dispenser (1) of FIG. 1 can be prepared by conventional injection molding using two mold halves—one with protrusions corresponding to those of the stamp (male mold half) and the other forming the base of the device (female mold half). The mold halves are juxtaposed to each other so as to form a cavity in the shape of the device (1) illustrated in FIG. 1. Injection of a monomer or reactive oligomer composition into this cavity followed by polymerization provides for a dispenser (1) now containing cavities (2) as per FIG. 1.

In embodiments, dispenser (1) can be fabricated in conjunction with assay device (20) to assure proper alignment of cavities (2) with wells (21).

Figure 2A:
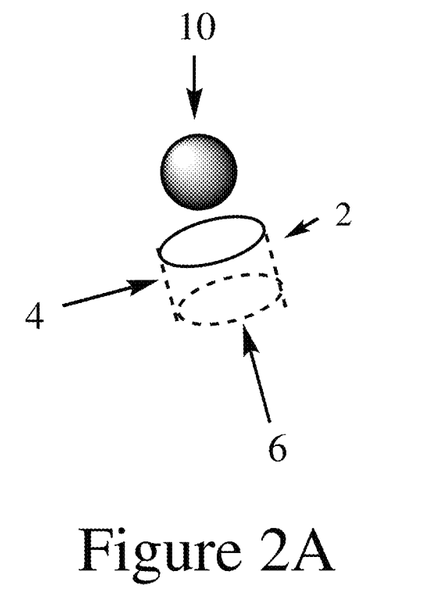
FIG. 2A illustrates cavity (2) sized to fit a single assay component (3) which for illustrative purposes is a substantially spherical bead (10).
Figure 2B:
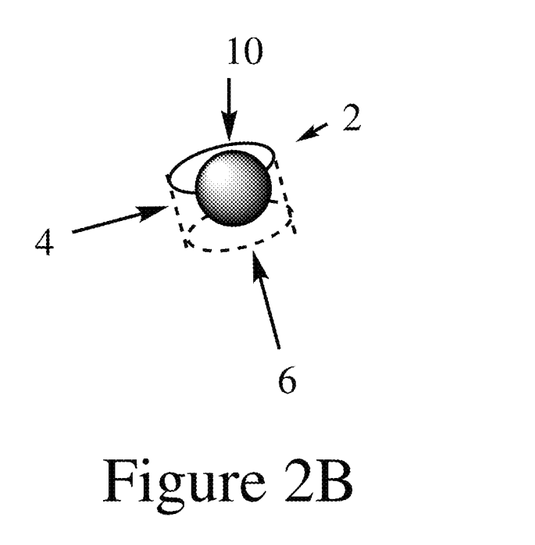
FIG. 2B illustrates insertion of bead (10) into cavity (2).

As to FIG. 2A, this figure illustrates a spherical bead (10) juxtaposed above cylindrical cavity (2) which is configured such that it is sized to fully fit bead (10). FIG. 2B illustrates spherical bead (10) inside of cavity (2) whereas FIG. 2C illustrates spherical bead (10) partially inside and partially outside cavity (2) where a sufficient amount of bead (10) is inside cavity (2) in a manner that retains said bead in said cavity.

Figure 2C:
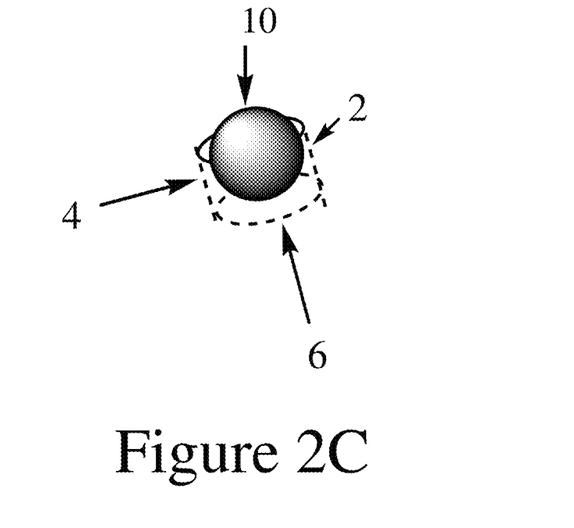
FIG. 2C illustrates that partial insertion of bead (10) into cavity (2) is sufficient to capture the bead.

In FIGS. 2A, 2B and 2C, the diameter (4) of cavity (2) is at least 100.1 percent of the diameter of spherical bead (10) (or expandable to at least such diameter) whereas the height of cavity (2) ranges from about 50 to about 115 percent of the diameter of bead (10). The use of cylindrical cavities (2) and spherical beads (10) prevents bead (10) from becoming lodged or jammed onto the surface of cavity (2) in a manner that prevents its release from dispenser (1).

Figure 3A:
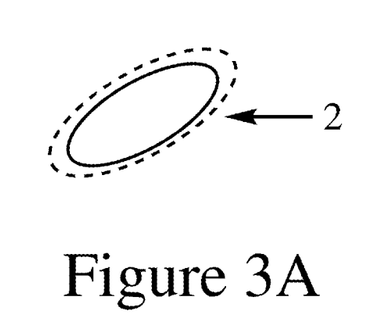
FIG. 3A illustrates the opening of cavity (2) in a dispenser where the dispenser comprises a reversibly expandable polymer in its expanded form.
Figure 3B:
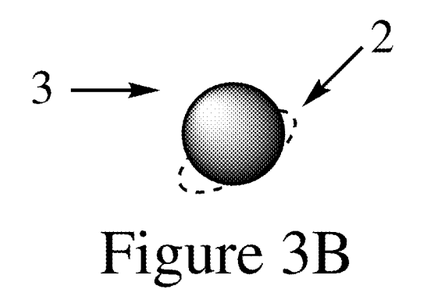
FIG. 3B illustrates assay component (3) overlaid onto said expanded cavity (2).
Figure 3C:
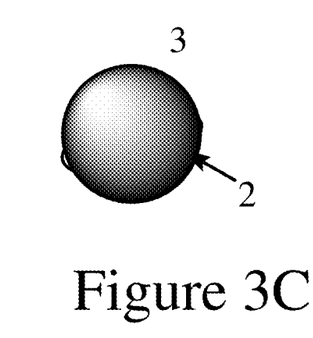
FIG. 3C illustrates assay component (3) fitted into the contracted cavity (2).

FIGS. 3A, 3B, and 3C illustrate insertion of bead (10) into a reversibly expandable polymer having cavity (2) that reversibly expands and contracts under suitable stimuli. FIG. 3A shows the relative size of cavity (2) both before expansion (solid circle) and after expansion (dashed circle). The size differential is exaggerated to illustrate the underlying concept.

FIG. 3B illustrates that bead (10) fits within expanded cavity (2).

FIG. 3C illustrates that upon reversing the expansion, cavity (2) shrinks around bead (10) holding it in place. To remove bead (10) from cavity (2), one merely applies the same stimulus to dispenser (1) previously used to expand cavity (2). In one preferred embodiment, the stimulus is a temperature change.

FIG. 4 illustrates yet another embodiment of dispenser (1) where a magnetic plate (9) is reversibly attached to its bottom surface (7). The magnetic plate (50) is used with magnetic beads (10) that are responsive to magnetic attraction as described above. As described previously, such magnetic beads (10) include those which are a composite of $Fe_3O_4$ and silica with an outer non-metallic coating that contains functionality that allows for attachment of a plurality of the same compound to its surface.

In one embodiment, beads (10) are loaded into dispenser (1) and then the magnetic plate (50) is inserted under the bottom (7) of dispenser (1). The addition of magnetic plate (50) to the dispenser (1) allows for retention of magnetic attracted beads (10) in cavities (2) while substantially eliminating any concern of displacement.

Loading

The loading of beads (10) into cavities (2) of dispenser (1) can be accomplished in any of a number of art recognized procedures. As shown in FIG. 5A, containment cap (30) comprises an inlet port (31) for introducing beads (10) and an outlet port (32) for recovering excess beads (10). Containment cap (30) is sized to fit over dispenser (1) and is aligned with dispenser (1) such that both inlet port (31) and outlet port (32) are aligned over dispenser (1).

In one preferred embodiment, containment cap (30) is sized and shaped to mate onto dispenser (1) in any number of well-known features including interlocking protrusions (33) extending upward from disperser (1) that extend into holes (34) in the body of containment cap (30). Alternatively, clips or other locking devices/configurations can be fitted onto either dispenser (1) or containment cap (30) that snap onto and lock both dispenser (1) and containment cap (30) into a fixed configuration. The specific locking mechanism is not critical.

A funnel-like cone (60) is sized such that the narrower end of that cone fits into inlet port (31) of containment cap (30) whereas the wider end of said cone allows for the addition of beads (10). Beads (10) are delivered either alone or in a fluid through inlet port (31) and onto the surface of dispenser (1) in a manner where beads (10) move from the inlet port (31) toward the outlet port (32). Beads (10) fill all cavities (2) and any excess beads are recycled through outlet port (32) for recycling into another dispenser (1).

In one embodiment, cone (60) is tilted so that beads (10) flow in a partially horizontal direction allowing the beads to fill cavities (2). In another embodiment, dispenser (1) is on a slight incline where the side adjacent to the inlet port (31) of containment cap (30) is higher than that of side adjacent to the outlet port (32) of containment cap (30). Such can be accomplished by applying a slight decline of at least about 1 degree as measured from the inlet port to the outlet port. Preferred declines of at from about at least 1 degree to about 10 degrees, and more preferably about 1 to 5 degrees, (or any value or subrange within the recited ranges, including endpoints) enable beads (10) to traverse the decline at such a rate that they are readily captured by cavities (2) in dispenser (1) while allowing excess beads (10) to be transmitted through the recovery port (32) and then captured. As shown in FIG. 5B, this process successfully allows a single bead (10) to be deposited into a single cavity (2) of dispenser (1) while allowing beads (10) not captured by cavities (2) to be recovered through outlet port (32).

It is noted that when a magnetically attractable bead (10) is used, a magnet (50) is placed under floor (7) of dispenser (1) after filling cavities (2) per the above process. As shown in FIG. 4, magnet (50) is preferably fitted and reversibly locked under dispenser (1) thereby allowing for retention of beads (10) with minimal risk of displacement of beads (10). The magnet used can be a permanent magnet or a reversible "on-off" magnet. As to a reversible magnet, it offers the advantage of controlling the magnetic attraction in a predictable manner.

It is further noted that when an expandable polymer-based dispenser (1) is used, empty dispenser (1) is first stimulated into its expanded state so that the cavities (2) can receive beads (10). After depositing beads (10) as per the above, the stimulus is removed and dispenser (1) reverts back to its non-expanded state thereby capturing the so deposited beads (10). Such capturing retains beads (10) in cavities (2).

Dispensing

Figure 6A:
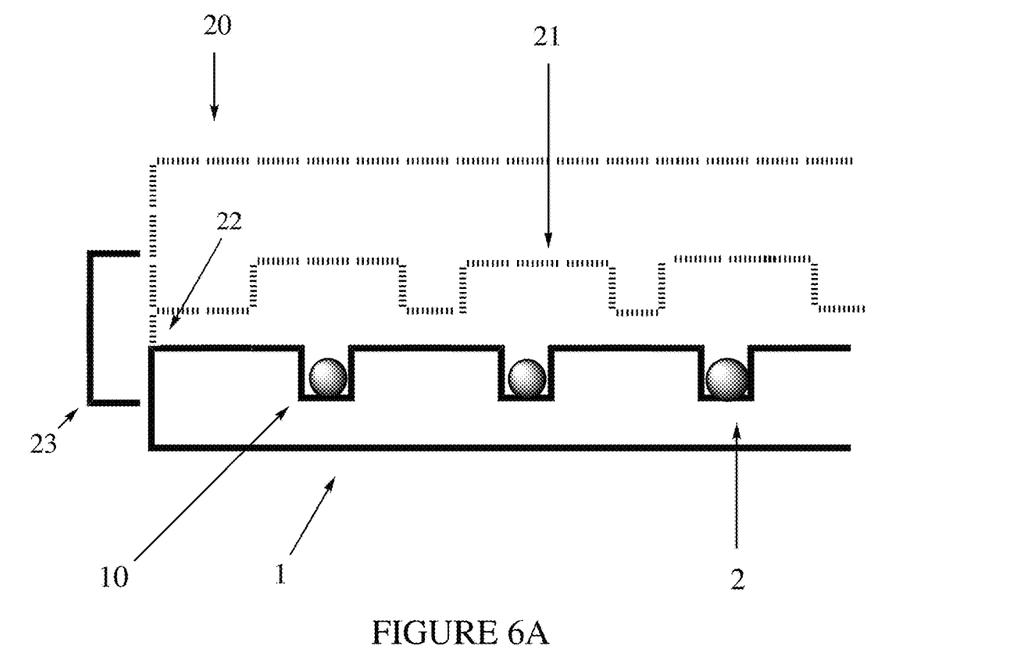
FIG. 6A illustrates integrating or fitting dispenser (1) with an assay device (20) to deliver beads (10) from cavities (2) to wells (21) of assay device (20). Alignment of dispenser (1) with assay device (20) can be facilitated with optional locking mechanism (23). When locked in place, dispenser (1) and assay device (20) need not be flush against each other. An optional gap (22) can be present, so long as gap (22) is smaller than the bead (10) or other assay components (3).
Figure 6A:
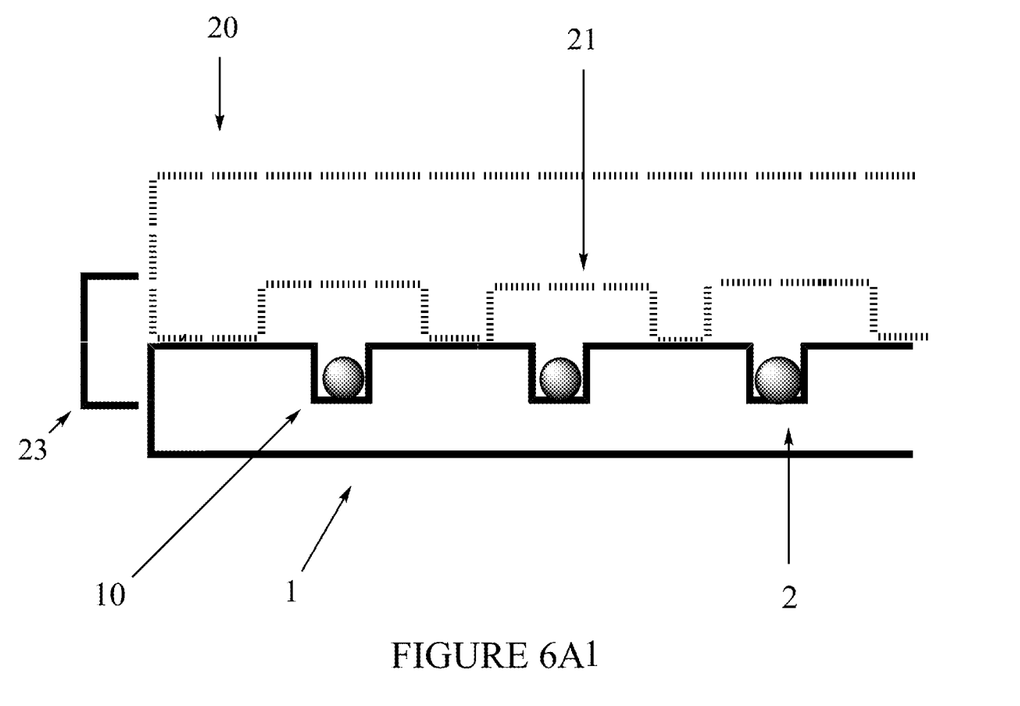
Figure 6B:
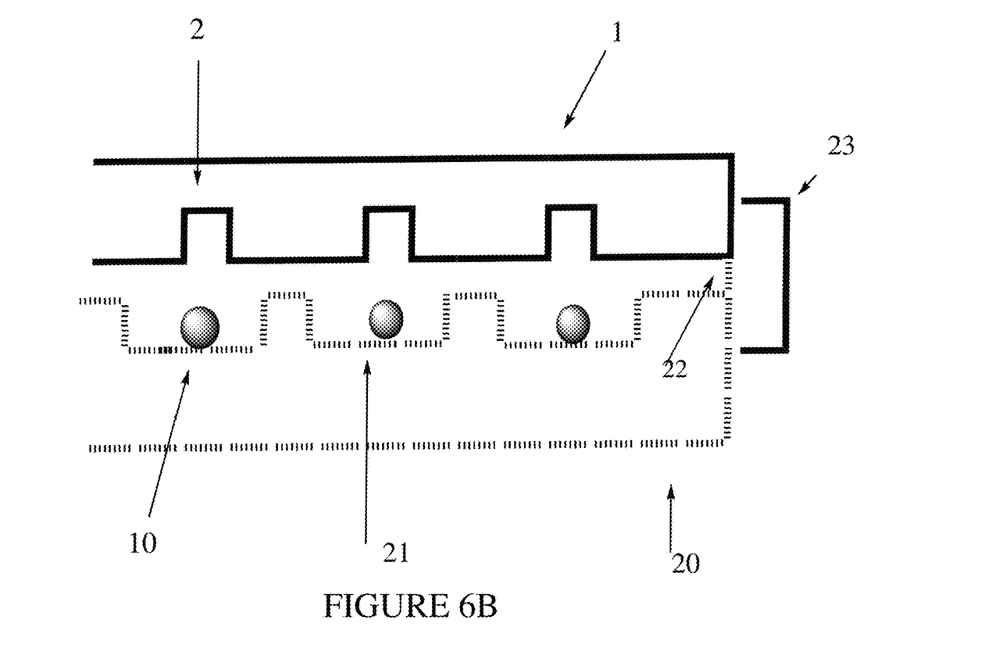
FIG. 6B illustrates the inversion of the setup in FIG. 6A and the delivery of beads (10) or other assay component (3) from dispenser (1) into wells (21) of assay device (20).

As before, each of cavities (2) on dispenser (1) are preselected to align with a single well (21) on assay device (20). As illustrated in FIGS. 6A and 6B, dispensing beads (10) into wells (21) is accomplished by placing assay device (20) over dispenser (1) and ensuring that each cavity (2) is aligned with a corresponding well (21). Dispenser (1) and assay device (20) are preferably locked into place by a conventional locking mechanism (23) which ensures that cavities (2) remain aligned with wells (21) during dispensing. Alignment can be confirmed by aligning markers (not shown) on device (20) with corresponding markers (not shown) on dispenser (1).

Figure 6B:
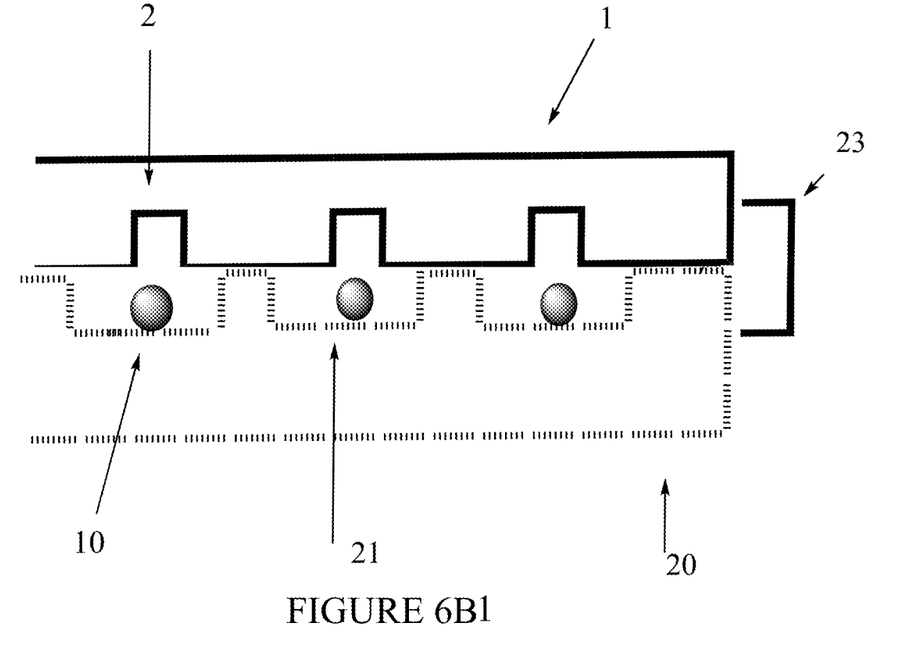

In FIG. 6A, an optional small gap (22) can be present between dispenser (1) and assay device (20) provided that the gap is less than the size of beads (10) and preferably about 50% or less than the size of beads (10). In some exemplary embodiments, as shown, for example, in FIGS. 6A1 and 6B1, dispenser (1) and assay device (20) are provided without the optional gap (22).

When alignment is confirmed, the combination of dispenser (1) and assay device (20) is merely flipped over so that dispenser (1) sits on top of assay device (20). For gravity-based release, a force or energy may be required, e.g. on the dispenser (1), to release beads (10) into wells (21). In one embodiment, the force or energy is at least 1 Newton or at least 0.01 Joule. Such can be applied by any method, e.g. tapping, vibration, sonication, centripetal force, temperature change, and the like. Because of the size distribution of the beads, some beads may be more tightly associated with the dispenser than others, and force (or additional force) may be required to dislodge them. The alignment of cavities (2) and wells (21) ensures that a single bead (10) is deposited into a single well (21).

For magnetically assisted retention of beads (10) in cavities (2), release of these beads (10) into wells (21) is achieved by first removing magnet (50) from dispenser (1) or reversing the magnetic attraction from an "on" position to an "off" position. If necessary, gentle tapping as described above can be used but only to the point that such is necessary.

For reversibly expandable retention of beads (10) in cavities (2), release of these beads (10) into wells (21) is achieved by first expanding cavities (2) by a stimulus that swells the polymer (e.g., change in temperature). When cavities (2) are expanded, release of beads (10) will proceed by gravity coupled with, as necessary, gentle tapping on dispenser (1) as described above.

Cells as the Assay Component

Another example of an assay component (3) is a cell which is used to evaluate its response to uptake of a test compound during an assay. The cell is added into dispenser (1) in a manner similar to bead (10) with the following caveats:

The diameter of cavity (2) is adjusted relative to the diameter of the cell such that only one cell can be added to each cavity (2). As human cells can range in diameter (4) from about 6 microns to more than about 50 microns, the diameter (4) of cavity (2) holding such cells preferably should range from about 3 to about 25 microns on the low side and from about 9 microns to about 75 microns on the high side (or any value or subrange within the recited ranges, including endpoints);

The height (5) of cavity (2) is adjusted relative to the height (5) of the cell such that only one cell can be added to each cavity (2). As human cells can range in height from about 6 microns to about 50 microns (for spherical human cells), the height (5) of cavity (2) ranges from about 6.01 microns to about 50.05 microns (or any value or subrange within the recited ranges, including endpoints);

The cells selected should be able to roll across the surface of dispenser (1); and The use of either magnetic attraction or reversibly expandable polymers are not preferred.

Otherwise, the cells are added to dispenser (1) and subsequently into assay device (20) in a manner substantially similar to that of beads (10).

In some cases, multiple copies of the same cell (50) are desired to be added to a single well (21) of assay device (20). In such cases, a separate dispenser (1) loaded with these cells (50) with a single cell per cavity (2). Cells (2) in this dispenser (1) are added to well (21) of assay device (30) in a manner similar to the first addition of cells (50). Likewise, the addition of other assay components (3) are similarly added.

Systems

In one embodiment, there is provided aa system for dispensing beads into an assay device. The system comprises:

a dispenser (1) comprising a multiplicity of cavities (2) wherein each cavity (2) is configured to reversibly hold only assay component(3) and further wherein dispenser (1) is configured to fit onto or over an assay device (20) which comprises a multiplicity of wells (21) such that each cavity (2) is aligned with a single well (21) so as to ensure that upon release of assay component (3) from the dispenser (1) only a single assay component (3) is deposited by a single cavity into a single well (21);

a containment cap equipped with an inlet for introducing an assay component into the cavities of the dispenser; and an assay device configured to be aligned with the dispenser to dispense the assay component into wells of the assay device.

The invention claimed is:

1. A device comprising:
   a) a transfer dispenser having a multiplicity of cavities wherein each cavity has an opening diameter and is configured to reversibly hold only a single bead, and
   b) an assay device which comprises a multiplicity of wells, wherein the assay device and the transfer dispenser are configured to fit onto or mate with each other, with a gap being present between said assay device and said transfer device, and wherein the cavities of the transfer dispenser are aligned with the wells of the device when the assay device and the transfer dispenser are fitted onto or mated with each other;
   wherein each well has an opening diameter that is larger than the opening diameter of each of said cavities such that, when each cavity is placed over each well, a containment space is formed comprising said cavity and said well;
   wherein the single bead is released from the cavity through said containment space and deposited into said well;
   wherein the beads are non-magnetic beads,
   wherein said gap has a size that is smaller than a size of the bead being transferred within the device, and
   wherein the transfer dispenser is configured to be inverted relative to the assay device.

2. The device of claim 1, wherein the transfer dispenser further comprises a locking mechanism that allows the transfer dispenser and the assay device to be locked into proper alignment.

3. The device of claim 1, wherein a diameter of the each of the cavities is reversibly expandable to accommodate the bead.

4. The device of claim 1, wherein a diameter of each of the cavities is at least 100.1% of the diameter of the bead, either in the native or expanded form to accommodate the bead.

5. The device of claim 1, wherein a depth of each of the cavities is at least 50% of the size of the bead up to about 125% of the size of the bead.

6. The device of claim 1, wherein the transfer dispenser is under the assay device.

7. The device of claim 6, wherein the transfer dispenser is over said assay device.

8. The device of claim 1, wherein the single bead is a size excluded bead such that the size of said bead excludes beads having a size that result in two beads fitting into a single cavity.

9. The device of claim 1, wherein the beads flow in a partially horizontal direction allowing the beads to fill the cavities.

10. The device of claim 1, wherein the beads have a size of from about 0.5 to about 100 microns.

11. The device of claim 1, wherein said device comprises the transfer dispenser having fitted thereon said assay device, and wherein said transfer dispenser is positioned below and aligned to the assay device in an inverted position such that each cavity in the transfer dispenser is aligned to a single well in the assay device provided that said transfer dispenser contains no more than a single bead in a given cavity.

12. The device of claim 1, wherein said device comprises the transfer dispenser having fitted thereto said assay device, and wherein said assay device is positioned below and aligned to the transfer dispenser such that each well in the assay device comprises a single bead, which is transferred from said transfer dispenser, and said transfer requires a single fitting of the assay device to the transfer dispenser.

13. A device comprising:
a) a transfer dispenser having a multiplicity of cavities wherein each cavity has a opening diameter and is configured to reversibly hold only a single bead, and
b) an assay device which comprises a multiplicity of wells, wherein the assay device and the transfer dispenser are configured to fit onto or mate with each other, optionally with a gap being present between said assay device and said transfer device, and wherein the cavities of the transfer dispenser are aligned with the wells of the device when the assay device and the transfer dispenser are fitted onto or mated with each other;

wherein each well has an opening diameter that is larger than the opening diameter of each of said cavities such that, when each cavity is placed over each well, a containment space is formed comprising said cavity and said well;

wherein the single bead is released from the cavity through said containment space and deposited into said well;

wherein the beads are non-magnetic beads;

wherein said gap when present has a size that is smaller than a size of the bead being transferred within the device, and wherein the transfer dispenser is configured to be inverted relative to the assay device.

14. The device of claim 13, wherein the device further comprises a locking mechanism that allows the transfer dispenser and the assay device to be locked into proper alignment.

15. The device of claim 13, wherein a diameter of each of the cavities is reversibly expandable to accommodate the bead.

16. The device of claim 13, wherein a diameter of each of the cavities is at least 100.1% of the diameter of the bead, either in the native or expanded form to accommodate the bead.

17. The device of claim 13, wherein a depth of each of the cavities is at least 50% of the size of the bead up to about 125% of the size of the bead.

18. The device of claim 13, wherein the transfer dispenser is under the assay device.

19. The device of claim 18, wherein the transfer dispenser is over said assay device.

20. The device of claim 13, wherein the single bead is a size excluded bead such that the size of said bead excludes beads having a size that result in two beads fitting into a single cavity.

21. The device of claim 13, wherein the beads flow in a partially horizontal direction allowing the beads to fill the cavities.

22. The device of claim 13, wherein the beads have a size of from about 0.5 to about 100 microns.

23. The device of claim 13, wherein said device comprises the transfer dispenser having fitted thereon said assay device, and wherein said transfer dispenser is positioned below and aligned to the assay device in an inverted position such that each cavity in the transfer dispenser is aligned to a single well in the assay device provided that said transfer dispenser contains no more than a single bead in a given cavity.

24. The device of claim 13, wherein said device comprises the transfer dispenser having fitted thereto said assay device, and wherein said assay device is positioned below and aligned to the transfer dispenser such that each well in the assay device comprises a single bead, which is transferred from said transfer dispenser, and said transfer requires a single fitting of the assay device to the transfer dispenser.

25. A device comprising:
a) a transfer dispenser having a multiplicity of cavities wherein each cavity has an opening diameter and is configured to reversibly hold only a single bead, and
b) an assay device which comprises a multiplicity of wells, wherein the assay device and the transfer dispenser are configured to fit onto or mate with each other, and wherein the cavities of the transfer dispenser are aligned with the wells of the device when the assay device and the transfer dispenser are fitted onto or mated with each other;

wherein each well has an opening diameter that is larger than the opening diameter of each of said cavities such that, when each cavity is placed over each well, a containment space is formed comprising said cavity and said well;

wherein the single bead is released from the cavity through said containment space and deposited into said well;

wherein the beads are non-magnetic beads;

wherein the transfer dispenser and the assay device are in direct contact with each other, and wherein the transfer dispenser is configured to be inverted relative to the assay device.

26. The device of claim 25, wherein the single bead is a size excluded bead such that the size of said bead excludes beads having a size that result in two beads fitting into a single cavity.

27. The device of claim 25, wherein the beads have a size of from about 0.5 to about 100 microns.

28. The device of claim 25, wherein said device comprises the transfer dispenser having fitted thereon said assay device, and
  wherein said transfer dispenser is positioned below and aligned to the assay device in an inverted position such that each cavity in the transfer dispenser is aligned to a single well in the assay device provided that said transfer dispenser contains no more than a single bead in a given cavity.

29. The device of claim 25, wherein said device comprises the transfer dispenser having fitted thereto said assay device, and
  wherein said assay device is positioned below and aligned to the transfer dispenser such that each well in the assay device comprises a single bead, which is transferred from said transfer dispenser, and said transfer requires a single fitting of the assay device to the transfer dispenser.

* * * * *